(12) United States Patent
Jankowiak et al.

(10) Patent No.: US 12,070,738 B2
(45) Date of Patent: Aug. 27, 2024

(54) SUPPORTED TANTALUM CATALYST FOR THE PRODUCTION OF 1,3-BUTADIENE

(71) Applicant: SYNTHOS DWORY 7 SPÓŁKA Z OGRANICZONĄ ODPOWIEDZIALNOŚCIĄ, Oswiecim (PL)

(72) Inventors: Ewelina Jankowiak, Imielin (PL); Szymon Skowronek, Wodzislaw Slaski (PL); Piotr Zapala, Zabrze (PL)

(73) Assignee: SYNTHOS DWORY 7 SPÓLKA Z OGRANICZONA ODPOWIEDZIALNOSCIA, Oswiecim (PL)

( * ) Notice: Subject to any disclaimer, the term of this patent is extended or adjusted under 35 U.S.C. 154(b) by 266 days.

(21) Appl. No.: 17/642,885

(22) PCT Filed: Sep. 15, 2020

(86) PCT No.: PCT/EP2020/075778
§ 371 (c)(1),
(2) Date: Mar. 14, 2022

(87) PCT Pub. No.: WO2021/052968
PCT Pub. Date: Mar. 25, 2021

(65) Prior Publication Data
US 2022/0395813 A1 Dec. 15, 2022

(30) Foreign Application Priority Data
Sep. 16, 2019 (EP) .................................... 19461582

(51) Int. Cl.
| | | |
|---|---|---|
| B01J 23/20 | (2006.01) | |
| B01J 21/08 | (2006.01) | |
| B01J 35/61 | (2024.01) | |
| B01J 37/02 | (2006.01) | |
| B01J 37/08 | (2006.01) | |
| C07C 1/207 | (2006.01) | |

(52) U.S. Cl.
CPC .............. *B01J 23/20* (2013.01); *B01J 21/08* (2013.01); *B01J 35/615* (2024.01); *B01J 35/617* (2024.01); *B01J 37/0213* (2013.01); *B01J 37/0236* (2013.01); *B01J 37/088* (2013.01); *C07C 1/2072* (2013.01); *C07C 2521/08* (2013.01); *C07C 2523/20* (2013.01)

(58) Field of Classification Search
CPC . B01J 23/20; B01J 21/08; B01J 35/615; B01J 35/617; B01J 37/0213; B01J 37/0236; B01J 37/088; B01J 23/04; B01J 35/00; B01J 35/30; B01J 37/0207; B01J 37/06; B01J 37/02; B01J 37/08; B01J 23/08; C07C 1/2072; C07C 2521/08; C07C 2523/20; C07C 2523/04; C07C 1/20; C07C 1/207; C07C 11/167
See application file for complete search history.

(56) References Cited

U.S. PATENT DOCUMENTS

| | | | |
|---|---|---|---|
| 2002/0055664 A1* | 5/2002 | Liu | .......................... C07C 45/33 585/658 |
| 2018/0201553 A1* | 7/2018 | Cadran | .................... B01J 23/20 |
| 2018/0208522 A1 | 7/2018 | Cadran et al. | |
| 2019/0105634 A1 | 4/2019 | Chinta et al. | |

FOREIGN PATENT DOCUMENTS

| | | |
|---|---|---|
| CN | 101049554 | 10/2007 |
| EP | 3 476 479 | 5/2019 |
| FR | 925617 | 9/1947 |
| JP | 6265410 | 1/2018 |
| WO | 2019081665 | 5/2019 |

OTHER PUBLICATIONS

International Search Report mailed Nov. 17, 2020, in connection with corresponding international Application No. PCT/EP2020/075778 (4 pp.).
Written Opinion of the International Searching Authority dated Nov. 17, 2020, in connection with corresponding international Application No. PCT/EP2020/075778 (8 pp.).
International Preliminary Report on Patentability mailed Dec. 20, 2021, in connection with corresponding international Application No. PCT/EP2020/075778 (17 pp.).
Ekaterina V. Makshina et al., "Review of old chemistry and new catalytic advances in the on-purpose synthesis of butadiene", Chemical Society Review, Issue 22, Mar. 6, 2014, 35 pp., at URL: DOI:10.1039/c4cs00105b.
D. Bayot et al., "Peroxo complexes of niobium(V) and tantalum(V)", Elsevier, ScienceDirect, Coordination Chemistry Reviews, 250 (2006) 2610-2626.
M. D. Jones et al., "Investigations into the conversion of ethanol into 1,3-butadiene", Catalysis Science & Technology, 2011, 1, 267-272.

(Continued)

*Primary Examiner* — Ali Z Fadhel
(74) *Attorney, Agent, or Firm* — NIXON & VANDERHYE P.C.

(57) ABSTRACT

The invention relates to a process for the production of 1,3-butadiene from a feed comprising ethanol and acetaldehyde in the presence of a supported tantalum catalyst obtainable by aqueous impregnation of the support with a water-soluble tantalum precursor. Furthermore, the present invention relates to a process for the production of a supported tantalum catalyst, and the supported tantalum catalyst. Finally, the invention relates to the use of the supported tantalum catalyst for the production of 1,3-butadiene from a feed comprising ethanol and acetaldehyde to increase one or both of selectivity and yield of the reaction.

24 Claims, No Drawings

(56) References Cited

OTHER PUBLICATIONS

Ho-Jeong Chae et al., "Butadiene production from bioethanol and acetaldehyde over tantalum oxide-supported ordered mesoporous silica catalysts", Elsevier, ScienceDirect, Applied Catalysis B: Environmental, 150-151 (2014) 596-604.

* cited by examiner

SUPPORTED TANTALUM CATALYST FOR THE PRODUCTION OF 1,3-BUTADIENE

The invention relates to a process for the production of 1,3-butadiene from a feed comprising ethanol and acetaldehyde in the presence of a supported tantalum catalyst obtainable by aqueous impregnation of the support with a water-soluble tantalum precursor. Furthermore, the present invention relates to a process for the production of a supported tantalum catalyst, and the supported tantalum catalyst. Finally, the invention relates to the use of the supported tantalum catalyst for the production of 1,3-butadiene from a feed comprising ethanol and acetaldehyde to increase one or both of selectivity and yield of the reaction.

1,3-Butadiene is one of the most important raw materials in the rubber industry, where it is used as a monomer in the production of synthetic rubbers like polybutadiene rubber (PBR), acrylonitrile-butadiene-styrene polymer (ABS), styrene-butadiene rubber (SBR), nitrile-butadiene rubber (NBR) and styrene-butadiene latex. Currently, 1,3-butadiene is mostly prepared from non-sustainable sources, like crude $C_4$ streams of steam cracking processes or by catalytic dehydrogenation of butane and butenes (*Chem. Soc. Rev.*, 2014, 43, 7917).

More recently, there has been increased interest in using ethanol as renewable source of 1,3-butadiene. M. D. Jones et al. (*Catal. Sci. Technol.*, 2011, 1, 267), for example, examined silica-supported binary and ternary catalytic systems for the conversion of ethanol to 1,3-butadiene. The highest selectivity to 1,3-butadiene of the examined systems was achieved using a $ZrO_x$—$ZnO/SiO_2$ catalyst doped with copper oxide giving a moderate yield of 1,3-butadiene of 30%.

In WO 2012/015340 A1, the one-step catalytic conversion of ethanol over silica-supported binary or ternary catalytic systems is reported. Doping of the zirconia-silica catalytic system with gold or silver and ceria, and using 9% of acetaldehyde in the feed and a WHSV of 0.3 $h^{-1}$, resulted in a 1,3-butadiene yield of 82% and 81%, respectively. Said catalytic systems, however, require the reduction of the gold and silver oxide contained therein before the one-step conversion of ethanol to 1,3-butadiene.

Starting from a mixture of ethanol and acetaldehyde, Ho-Jeong Chae et al. (*Appl. Catal. B*, 2014, 150-151, 596) obtained a 1,3-butadiene yield of 37% when using a tantalum oxide catalyst on SBA-15 as support. The catalyst was synthesized by impregnation of the support with an ethanolic solution of tantalum chloride. The disadvantage of this method is the requirement to perform the synthesis under anhydrous conditions, because tantalum chloride is prone to hydrolysis in the presence of even small amounts of water.

US 2019/0105634 A1 inter alia relates to a process comprising reacting a feed stream containing ethanol and optionally acetaldehyde in a dehydration reactor in the presence of a dehydration catalyst system having a group 5 metal oxide and a zeolite support and obtaining a product stream comprising 1,3-butadiene from the dehydration reactor. A tantalum oxide catalyst was prepared by impregnation of a silica support in an ethanolic solution of tantalum chloride. Using the obtained catalyst comprising 2 wt % tantalum oxide supported on silica in said process, however, only lead to yields of 1,3-butadiene of between 2.1 and 8.1% depending on the reaction conditions.

EP 3 476 479 A1 discloses the preparation of aqueous tantalum peroxo complex solutions by precipitating $Ta_2O_5 \cdot xH_2O$ from $H_2[TaF_7]$ with the aid of ammonia. The obtained solid is dissolved in a mixture of tetramethyl ammonium hydroxide (TMAOH), hydrogen peroxide and water. The aqueous tantalum peroxo complex solution is used in the in situ generation of silica-supported tantalum catalysts (e.g. a Ta(6.8%)/MCM41 catalyst) with high BET specific surface areas. For 1,3-butadiene production from ethanol, a Cu(10%)/Ta(6.8%)/MCM41 catalyst is prepared by incipient wetness impregnation of Ta(6.8%)/MCM41 with $Cu(NO_3)_2 \times 2.5H_2O$.

JP 2015071128 A relates to the photo-deposition of various metal oxides/hydroxides other than CrO as a shell for preventing a reverse reaction due to oxygen reduction on a photocatalyst for water splitting. A photocatalyst for water splitting is put into a water-soluble transition metal (Ti, Nb, or Ta) peroxo complex solution and irradiated with light. This reduces the peroxo complexes so that the metal oxide/hydroxide in the complexes coat the photocatalyst surface. The water splitting rates achieved by the photocatalyst supporting the shell of Ti, Nb, or Ta oxide was measured. The photocatalysts produced in JP 2015071128 A are not used in the production of 1,3-butadiene and no drying or calcination steps are performed after the deposition of the water-soluble transition metal peroxo complexes onto the photocatalyst.

Hence, there is a continuing need for providing straightforward processes for the production of supported metal oxide catalysts that enable the production of 1,3-butadiene with high yield and selectivity.

SUMMARY OF THE INVENTION

According to the present invention, it was surprisingly found that a supported tantalum catalyst prepared by aqueous impregnation of a support with a water-soluble tantalum precursor (as described herein) leads to improved selectivity to and yield of 1,3-butadiene.

Thus, in a first aspect, the present invention relates to a process for the production of 1,3-butadiene, the process comprising i) contacting a feed comprising ethanol and acetaldehyde with a supported tantalum catalyst to obtain a raw product comprising 1,3-butadiene, wherein the catalyst is obtainable (or obtained) by a process comprising a) preparing a water-soluble tantalum precursor by reacting one or more tantalum compound(s) in aqueous solution and under oxidative conditions, b) aqueous impregnating a support with the water-soluble tantalum precursor obtained from step a), c) drying, and d) calcination.

In a second aspect, the present invention relates to a process for the production of a supported tantalum catalyst, comprising the steps of a) preparing a water-soluble tantalum precursor by reacting one or more tantalum compound(s) in aqueous solution and under oxidative conditions, b) aqueous impregnating a support with the water-soluble tantalum precursor obtained from step a), c) drying, and d) calcination.

Moreover, in a third aspect, the invention relates to a supported tantalum catalyst as obtainable (or obtained) according to the process of the second aspect.

Finally, and in a fourth aspect, the invention relates to the use of the supported tantalum catalyst according to the third aspect for the production of 1,3-butadiene from a feed comprising ethanol and acetaldehyde, to increase one or both of x. selectivity and y. yield of the reaction to 1,3-butadiene.

DETAILED DESCRIPTION OF THE INVENTION

1) Process for the Production of 1,3-Butadiene

The process for the production of 1,3-butadiene of the present invention comprises the following steps
  i) contacting a feed comprising ethanol and acetaldehyde with a supported tantalum catalyst to obtain a raw product comprising 1,3-butadiene,
  wherein the catalyst is obtainable (or obtained) by a process comprising
    a) preparing a water-soluble tantalum precursor by reacting one or more tantalum compound(s) in aqueous solution and under oxidative conditions,
    b) aqueous impregnating a support with the water-soluble tantalum precursor obtained from step a),
    c) drying (the product of step b)), and
    d) calcination (of the product of step c)).

In one preferred embodiment, the supported tantalum catalyst has a tantalum content, calculated as $Ta_2O_5$ and based on the total weight of the catalyst, in a range of from 0.1 to 10 wt %, preferably from 0.5 to 5 wt %, more preferably from 2 to 3 wt %. Most preferably, the supported tantalum catalyst has a tantalum content, calculated as $Ta_2O_5$ and based on the total weight of the catalyst, of about 3 wt %.

Preferably, the tantalum compound is selected from the group consisting of tantalum halides, tantalum hydroxide and tantalum oxalate, preferably from the group consisting of tantalum (V) hydroxide and tantalum (V) chloride, more preferably the tantalum compound is tantalum (V) hydroxide.

Another preferred embodiment relates to a process as defined herein, wherein the i) contacting takes place at a temperature in a range of from 200 to 500° C., preferably from 250 to 450° C., more preferably from 300 to 400° C.

Moreover, preferably the i) contacting takes place at a weight hourly space velocity in a range of from 0.2 to 10 $h^{-1}$, preferably from 1 to 7 $h^{-1}$.

Preferred is a process as defined herein, further comprising ii) separating the raw product at least into a first portion comprising 1,3-butadiene, a second portion comprising acetaldehyde and a third portion comprising ethanol, and preferably at least part of the second, of the third, or of the second and of the third portions is recycled into the feed. Preferably, all of the second, of the third, or of the second and of the third portions is recycled into the feed.

Another preferred embodiment relates to a process as defined herein, wherein the i) contacting takes place in a continuous flow fixed bed reactor.

2) Process for the Production of a Supported Tantalum Catalyst

As set out above, according to another aspect the invention relates to a process for the production of a supported tantalum catalyst, comprising the steps of
a) preparing a water-soluble tantalum precursor by reacting one or more tantalum com-pound(s) in aqueous solution and under oxidative conditions,
b) aqueous impregnating a support with the water-soluble tantalum precursor obtained from step a),
c) drying (the product of step b)), and
d) calcination (of the product of step c)).

In one preferred embodiment, the supported tantalum catalyst obtainable or obtained by the process according to the invention as defined herein has a tantalum content, calculated as $Ta_2O_5$ and based on the total weight of the catalyst, in a range of from 0.1 to 10 wt %, preferably from 0.5 to 5 wt %, more preferably from 2 to 3 wt %. Most preferably, the supported tantalum catalyst has a tantalum content, calculated as $Ta_2O_5$ and based on the total weight of the catalyst, of about 3 wt %.

Preferably, the tantalum compound reacted in step a) of the process is selected from the group consisting of tantalum halides, tantalum hydroxide and tantalum oxalate, preferably from the group consisting of tantalum (V) hydroxide and tantalum (V) chloride, more preferably the tantalum compound is tantalum (V) hydroxide.

Preferably, the reacting in aqueous solution and under oxidative conditions comprises the presence of one or both of persulfate ion and hydrogen peroxide. More preferably, the reacting in aqueous solution and under oxidative conditions comprises the presence of hydrogen peroxide.

In order to provide for persulfate ions in aqueous solution, ammonium persulfate is a preferred starting material. When using sodium and/or potassium persulfate, these cations should be removed from the supported tantalum catalyst before the calcination step d). Sodium and potassium removal can take place before or after the drying step c) of the process of the invention, and is preferably achieved by washing the (dried) impregnated support with one or more organic and/or inorganic acid(s).

Preferably, the combined content of the supported tantalum catalyst, in sodium and potassium, is less than 0.05 wt. % (based on the total weight of the catalyst) after the calcination step d). Preferably, sulfur should also be removed from the catalyst, preferably at elevated temperatures in the form of sulfur oxides, preferably in the drying and calcination processes (as described below).

The use of a basic metal peroxide, in order to generate hydrogen peroxide in the aqueous solution may lead to generation of the pH greater than 7, e.g. sodium peroxide hydrolyzes in a vigorous reaction to sodium hydroxide and hydrogen peroxide.

In case the water-soluble tantalum compound(s) is/are reacted with aqueous sodium hydroxide in step a) (or step a1) or step a2)) of the process as defined herein, sodium has to be removed from the supported tantalum catalyst before calcination step d). The sodium removal can take place before or after drying step c) of the process as defined herein, and preferably is achieved by washing the (dried) impregnated support with one or more organic and/or inorganic acid(s). Preferably, the sodium content of the obtained supported tantalum catalyst after calcination step d) is less than 0.05 wt. %, based on the total weight of the catalyst.

Preferably, the water-soluble tantalum precursor is prepared by reacting at a pH of the aqueous solution of greater than 7, in step a) of the process according to the invention.

In one preferred embodiment of the process as defined herein, the water-soluble tantalum precursor is prepared by
a1) reacting said tantalum compound(s) with aqueous hydrogen peroxide, followed by reaction with one or both of aqueous ammonia and aqueous sodium hydroxide; or
a2) reacting said tantalum compound(s) simultaneously with aqueous hydrogen peroxide and one or both of aqueous ammonia and aqueous sodium hydroxide.

Preferably, the weight ratio of tantalum to ammonia is in a range of from 3:1 to 1:1, the weight ratio referring to tantalum as a metal and pure ammonia, preferably is about 2:1, the respective weight ratio referring to tantalum as a metal and pure ammonia.

According to another preferred embodiment, the weight ratio of tantalum to hydrogen peroxide in step a) or step a1)

or step a2) is in a range of from 1:10 to 1:40, the weight ratio referring to tantalum as a metal and pure hydrogen peroxide, preferably is about 1:20.

In case the water-soluble tantalum compound(s) is/are reacted with aqueous sodium hydroxide in step a) or step a1) or step a2) of the process as defined herein, sodium has to be removed from the supported tantalum catalyst before the calcination step d). The sodium removal can take place before or after drying step c) of the process as defined herein, and preferably is achieved by washing the (dried) impregnated support with one or more organic and/or inorganic acid(s). Preferably, the sodium content of the obtained supported tantalum catalyst after calcination step d) is less than 0.05 wt. %, based on the total weight of the catalyst.

Hence, a preferred embodiment of the process as defined herein comprises (besides steps a) and b)) the steps of c) drying (the product of step b)), and
c') sodium removal (from the product of step c)), and
d) calcination (of the product of step c')).

A preferred alternative embodiment of the process as defined herein comprises (besides steps a) and b)) the steps of c') sodium removal (from the product of step b)), and
c) drying (the product of step c')), and
d) calcination (of product of step c)).

According to a preferred alternative embodiment of the process as defined herein, step b) of the process, the aqueous impregnation of the support with the tantalum precursor obtained from step a), further comprises the simultaneous impregnation of the support with an aqueous solution of one or more caesium compound(s). Preferably, the caesium com-pound(s) is/are one or more organic or inorganic salts. More preferably, the caesium com-pound(s) is/are selected from the group consisting of caesium nitrate, caesium formate, caesium oxalate, caesium carbonate, caesium hydroxide and caesium acetate.

Hence, according to a preferred alternative embodiment of the process as defined herein, step b) comprises or consists of b) aqueous impregnating a support with the water-soluble tantalum precursor obtained from step a) and, preferably simultaneously, with one or more caesium compound(s) (as defined herein).

According to another preferred alternative embodiment of the process as defined herein, the caesium compound(s) as defined herein can be reacted together with the tantalum compound(s) as defined herein in step a) or a1) or a2) of the process as defined herein. Preferably, the supported tantalum catalyst obtainable or obtained by the process as defined herein has a caesium content, calculated as $Cs_2O$ and based on the total weight of the catalyst, in a range of from 0.02 to 1.5 wt %, preferably from 0.05 to 1 wt %, more preferably from 0.1 to 0.5 wt %, and/or preferably the weight ratio of $Cs_2O$ to $Ta_2O_5$ in the catalyst is in a range of from 1:6 to 1:30.

Without wishing to be bound to any particular theory, functionalization of the catalyst with caesium appears to lead to the blocking of highly acidic centres, which are responsible for the production of side products of the conversion of ethanol and acetaldehyde to 1,3-butadiene such as ethylene and diethyl ether. Another advantage of caesium doping of the supported tantalum catalyst is connected with the possibility to perform the process for the production of 1,3-butadiene as defined herein at higher temperatures, where higher con-versions without any significant loss of selectivity or even an increase in selectivity are obtained and therefore higher yields can be achieved.

Preferably, the support is selected from ordered and non-ordered porous silica supports, aluminosilicate supports and other porous oxide-supports and mixtures thereof, more preferably from $Al_2O_3$, $ZrO_2$, $TiO_2$, MgO, ZnO, NiO, $CeO_2$, clays and mixtures thereof.

The support that is impregnated in step b) of the processes of the present invention may be synthesised or may be purchased from commercial suppliers.

Preferably, the support as defined herein has a specific surface area (SSA) in a range of from 130-550 $m^2/g$, more preferably in a range of from 190 to 280 $m^2/g$. Within the frame-work of the present text, the term "specific surface area" means the BET specific surface area (in $m^2/g$) determined by the single-point BET method according to ISO 9277:2010, complemented by, if applicable, ISO 18757: 2003.

Preferably, the support as defined herein has an average pore diameter of 30-300 Å (determined by the method of Barrett, Joyner and Halenda).

Preferably, the support as defined herein has a pore volume of 0.2-1.5 ml/g (determined by the method of Barrett, Joyner and Halenda).

More preferably, the support as defined herein has a specific surface area of 130-550 $m^2/g$, most preferably of 190 to 280 $m^2/g$, and an average pore diameter of 30-300 Å and a pore volume of 0.2-1.5 ml/g.

Reacting one or more tantalum compound(s) as defined herein with hydrogen peroxide and ammonia in step a), a1) or a2) of the process as defined herein is particularly advantageous since said compounds are readily commercially available, can be easily removed after impregnation step b) by thermal treatment during calcination step d) of the process and do not change the chemical nature of the surface of the supported catalyst.

Moreover, the catalyst preparation process in aqueous solution according to the present invention comprising the preparation of a water-soluble tantalum precursor from one or more tantalum compound(s) advantageously allows for better dispersion of $TaO_x$ sites on the surface of the support and thus provides higher selectivity towards 1,3-butadiene.

Hence, the aqueous impregnation of a support with the water-soluble tantalum precursor obtained from step a) preferably takes place in a fully homogeneous aqueous solution in step b) of the process according to the invention.

It is well known that tantalum (V) chloride is moisture sensitive and difficult to handle and usually hydrolyzes in water with the formation of precipitate. However, in the process according to the invention as defined herein, a water-soluble tantalum precursor is prepared in step a) of the process, e.g. by using hydrogen peroxide and ammonia as complexing agents. After an optional step of diluting the water-soluble tantalum precursor obtained from step a) of the process to an appropriate concentration with water, it is used to impregnate the support in step b) of the process. Various tantalum compounds as defined herein, including tantalum (V) chloride, can be used for the preparation of the water-soluble tantalum precursor in step a) of the process as defined herein. Particularly preferred, however, is the use of tantalum (V) hydroxide in step a) of the process as defined herein, because the production of corrosive gases and a strongly exothermic reaction are avoided.

According to a preferred embodiment of the process according to the invention as defined herein, additional water is added to the partly or preferably completely dissolved water-soluble tantalum precursor obtained from step a) between steps a) and b) of the process, preferably to adjust the volume of the impregnating solution to the pore volume of the support that is impregnated in step b).

According to another preferred embodiment of the process according to the invention as defined herein, the support as defined herein is washed with one or more organic or inorganic acid(s), optionally followed by heat treatment, before it is impregnated in step b) with the water-soluble tantalum precursor obtained from step a) and optionally one or more caesium salts (as defined herein).

3) Supported Tantalum Catalyst

According to another aspect, the invention relates to a supported tantalum catalyst as obtainable (or obtained) by a process as defined herein.

In one preferred embodiment of the supported catalyst as defined herein, the support is selected from ordered and non-ordered porous silica supports, aluminosilicate supports and other porous oxide-supports and mixtures thereof, more preferably from $Al_2O_3$, $ZrO_2$, $TiO_2$, MgO, ZnO, NiO, $CeO_2$, clays and mixtures thereof.

Preferably, the support as defined herein has a specific surface area of 130-550 $m^2/g$, more preferably of 190 to 280 $m^2/g$.

Preferably, the support as defined herein has an average pore diameter of 30-300 Å.

Preferably, the support as defined herein has a pore volume of 0.2-1.5 ml/g.

More preferably, the support as defined herein has a specific surface area of 130-550 $m^2/g$, most preferably of 190 to 280 $m^2/g$, and an average pore diameter of 30-300 Å and a pore volume of 0.2-1.5 ml/g.

Preferably, the supported tantalum catalyst has a tantalum content, calculated as $Ta_2O_5$ and based on the total weight of the catalyst, in a range of from 0.1 to 10 wt %, preferably from 0.5 to 5 wt %, more preferably from 2 to 3 wt %. Most preferably, the supported tantalum catalyst has a tantalum content, calculated as $Ta_2O_5$ and based on the total weight of the catalyst, of about 3 wt %.

Preferably, the supported tantalum catalyst as defined herein further comprises caesium, preferably the caesium content of the catalyst, calculated as $Cs_2O$ and based on the total weight of the catalyst, is in a range of from 0.02 to 1.5 wt %, preferably from 0.05 to 1 wt %, more preferably from 0.1 to 0.5 wt %, and/or preferably the weight ratio of $Cs_2O$ to $Ta_2O_5$ in the catalyst is in a range of from 1:6 to 1:30.

4) Use of the Supported Tantalum Catalyst

In another aspect, the present invention relates to the use of a supported tantalum catalyst as defined herein for the production of 1,3-butadiene from a feed comprising ethanol and acetaldehyde, to increase one or both of x. selectivity and y. yield of the reaction to 1,3-butadiene.

Preferred embodiments of the process for the production of 1,3-butadiene according to the invention correspond to or can be derived from the preferred embodiments of the process for the production of a supported tantalum catalyst according to the invention or vice versa. Moreover, preferred embodiments of the processes according to the invention correspond to or can be derived from the preferred embodiments of the supported tantalum catalyst or use according to the invention which are explained above or vice versa.

The following examples show the advantages of the present invention. Unless noted otherwise, all percentages are given by weight.

EXAMPLES

1. Preparation of the Supported Catalysts

Tantalum chloride 99,99% was supplied by Acros Organics. Moist tantalum hydroxide, also referred to as $Ta_2O_5*nH_2O$ and having a composition of about 40 to about 50 wt. % of $Ta_2O_5$, was supplied by H.C. Starck (trade name "Tantalum Oxihydrate moist").

Silica CARiACT Q-15 and Q-10 was supplied by Fuji Silysia Chemical LTD. CARiACT Q-15 is a spherical silica catalyst support with a particle size of 1.18-2.36 mm, a bulk density of 0.43 g/ml, an average pore diameter of 150 Å, a pore volume of 0.99 ml/g and a specific surface area of 190 $m^2/g$. CARiACT Q-10 is a spherical silica catalyst support with a particle size of 1.18-2.36 mm, a bulk density of 0.43 g/ml, an average pore diameter of 100 Å, a pore volume of 0.99 ml/g and a specific surface area of 280 $m^2/g$.

The preparation of the supported catalysts for Examples 1 to 8 was conducted as follows:

1a) Comparative Example 1

The catalyst for Comparative Example 1 with a composition of 3 wt % $Ta_2O_5/SiO_2$ was prepared based on the teaching of Chae et al. (*Appl. Catal. B*, 2014, 150-151, 596) using tantalum (V) chloride as tantalum compound and absolute ethanol as solvent. The specific surface area of the silica support was 280 $m^2/g$.

1b) Examples 2 and 3 According to the Invention

Because the tantalum hydroxide as supplied is moist, thermogravimetric analysis was performed before the synthesis to estimate the concentration of tantalum pentoxide contained in the compound. In this case, the tantalum pentoxide concentration was 47.4 wt % so that 45 g of CARiACT Q-10 silica support (as described above) were impregnated at room temperature with 50 $cm^3$ of a solution obtained as described below by dropping portions of the impregnation solution on the support.

The impregnation solution was obtained by first treating 2.94 g of tantalum hydroxide with 41 $cm^3$ 30% aqueous solution of hydrogen peroxide followed by addition of 4.1 $cm^3$ 25% aqueous solution of ammonia. After complete dissolution water was added to obtain 50 $cm^3$ of the solution.

The obtained impregnated support was dried at 120° C. for 10 h and subsequently calcined at 500° C. for 5 h with heating rate 5° C./min in air atmosphere.

1c) Examples 4 and 5 According to the Invention

Because the tantalum hydroxide as supplied is moist, thermogravimetric analysis was performed before the synthesis to estimate the concentration of tantalum pentoxide contained in the compound. In this case, the tantalum pentoxide concentration was 47.4 wt % so that 45 g of CARiACT Q-15 silica support (as described above) were impregnated at room temperature with 50 $cm^3$ of a solution obtained as described below by dropping portions of the impregnation solution on the support.

The impregnation solution was obtained by first treating 2.94 g of tantalum hydroxide with 41 $cm^3$ 30% aqueous solution of hydrogen peroxide followed by addition of 4.1 $cm^3$ 25% aqueous solution of ammonia. After complete dissolution water was added to obtain 50 $cm^3$ of the solution.

The obtained impregnated support was dried at 120° C. for 10 h and subsequently calcined at 500° C. for 5 h with heating rate 5° C./min in air atmosphere.

1d) Example 6 According to the Invention

Because the tantalum hydroxide as supplied is moist, thermogravimetric analysis was performed before the synthesis to estimate the concentration of tantalum pentoxide contained in the compound. In this case, the tantalum pentoxide concentration was 47.4 wt % so that 45 g of CARiACT Q-10 silica support (as described above) were impregnated at room temperature with 50 cm³ of a solution obtained as described below by dropping portions of the impregnation solution on the support.

The impregnation solution was obtained by first treating 2.94 g of tantalum hydroxide and 0.06 g of caesium formate with 41 cm³ 30% aqueous solution of hydrogen peroxide followed by addition of 4.1 cm³ 25% aqueous solution of ammonia. After complete dissolution water was added to obtain 50 cm³ of the solution.

The obtained impregnated support was dried at 120° C. for 10 h and subsequently calcined at 500° C. for 5 h with heating rate 5° C./min in air atmosphere.

1e) Example 7 According to the Invention

Because the tantalum hydroxide as supplied is moist, thermogravimetric analysis was performed before the synthesis to estimate the concentration of tantalum pentoxide contained in the compound. In this case, the tantalum pentoxide concentration was 47.4 wt % so that 45 g of CARiACT Q-10 silica support (as described above) were impregnated at room temperature with 50 cm³ of a solution obtained as described below by dropping portions of the impregnation solution on the support.

The impregnation solution was obtained by first treating 2.94 g of tantalum hydroxide and 0.29 g of caesium formate with 41 cm³ 30% aqueous solution of hydrogen peroxide followed by addition of 4.1 cm³ 25% aqueous solution of ammonia. After complete dissolution water was added to obtain 50 cm³ of the solution.

The obtained impregnated support was dried at 120° C. for 10 h and subsequently calcined at 500° C. for 5 h with heating rate 5° C./min in air atmosphere.

1f) Example 8 According to the Invention

Because the tantalum hydroxide as supplied is moist, thermogravimetric analysis was performed before the synthesis to estimate the concentration of tantalum pentoxide contained in the compound. In this case, the tantalum pentoxide concentration was 47.4 wt % so that 45 g of CARiACT Q-15 silica support (as described above) were impregnated at room temperature with 50 cm³ of a solution obtained as described below by dropping portions of the impregnation solution on the support.

The impregnation solution was obtained by first treating 2.94 g of tantalum hydroxide and 0.06 g of caesium formate with 41 cm³ 30% aqueous solution of hydrogen peroxide followed by addition of 4.1 cm³ 25% aqueous solution of ammonia. After complete dissolution water was added to obtain 50 cm³ of the solution.

The obtained impregnated support was dried at 120° C. for 10 h and subsequently calcined at 500° C. for 5 h with heating rate 5° C./min in air atmosphere.

2. Catalytic Tests

Comparative Example 1

The catalyst synthesized using absolute ethanol as solvent (as described above) was placed in a continuous flow stainless steel reactor. The reactor was heated to 350° C., at a nitrogen flow rate of 20 ml/min. The reaction was carried out using 96% ethanol-acetaldehyde mixture at a volumetric ratio 2.5:1 as a feed with a weight hourly space velocity (WHSV) of 1 h⁻¹.

The results were calculated as follows and are indicated in Table 1 below:

$$Conversion = \frac{mass\ of\ the\ converted\ reactant}{mass\ of\ the\ feed} \cdot 100$$

$$Selectivity = \frac{C\ moles\ in\ 1,3-butadiene}{C\ moles\ in\ all\ products} \cdot 100$$

$$Yield = \frac{Conversion \cdot Selectivity}{100}$$

Example 2

The reaction was carried out as in Example 1, except that the catalyst was prepared using a water-soluble tantalum precursor that was obtained from tantalum hydroxide as described above.

Example 3

The reaction was carried out as in Example 2, except that the reactor was heated to 375° C.

Example 4

The reaction was carried out as in Example 2, except that the catalyst was prepared using silica with a specific surface area of 190 m²/g as described above.

Example 5

The reaction was carried out as in Example 4, except that the reactor was heated to 375° C.

Example 6

The reaction was carried out as in Example 3, except that the catalyst was 0.1% $Cs_2O$-3% $Ta_2O_5/SiO_2$ (prepared as described above).

Example 7

The reaction was carried out as in Example 6, except that the catalyst was 0.5% $Cs_2O$-3% $Ta_2O_5/SiO_2$ (prepared as described above).

Example 8

The reaction was carried out as in Example 5, except that the catalyst was 0.1% $Cs_2O$-3% $Ta_2O_5/SiO_2$ (prepared as described above).

TABLE 1

| Ex. | Final catalyst | Loading [wt %][1] | | Silica SSA [m²/g] | Tantalum catalyst precursor used | Solvent in catalyst preparation | T[° C.] | C[%] | 1,3-BD | |
|---|---|---|---|---|---|---|---|---|---|---|
| | | Cs₂O | Ta₂O₅ | | | | | | S[%] | Y[%] |
| 1* | TaO$_x$/SiO$_2$ | 0 | 3 | 280 | Chloride | Ethanol | 350 | 49 | 75 | 37 |
| 2 | TaO$_x$/SiO$_2$ | 0 | 3 | 280 | Hydroxide | Water | 350 | 51 | 80 | 41 |
| 3 | TaO$_x$/SiO$_2$ | 0 | 3 | 280 | Hydroxide | Water | 375 | 57 | 72 | 41 |
| 4 | TaO$_x$/SiO$_2$ | 0 | 3 | 190 | Hydroxide | Water | 350 | 50 | 77 | 39 |
| 5 | TaO$_x$/SiO$_2$ | 0 | 3 | 190 | Hydroxide | Water | 375 | 63 | 69 | 43 |
| 6 | CsO$_x$—TaO$_x$/SiO$_2$ | 0.1 | 3 | 280 | Hydroxide | Water | 375 | 57 | 73 | 42 |
| 7 | CsO$_x$—TaO$_x$/SiO$_2$ | 0.5 | 3 | 280 | Hydroxide | Water | 375 | 52 | 75 | 39 |
| 8 | CsO$_x$—TaO$_x$/SiO$_2$ | 0.1 | 3 | 190 | Hydroxide | Water | 375 | 58 | 76 | 44 |

Ex. = Example (* = Comparative)
SSA = Specific surface area
T = Temperature
C = Conversion
S = Selectivity
Y = Yield per pass (with no recirculation of the unreacted feed)
1,3-BD = 1,3-butadiene
[1]The numbers are weight % of metal oxide as indicated based on the total weight of the catalyst Comparing Example 1 (comparative) to Examples 2 to 8 shows that the use of the supported tantalum catalysts prepared according to the present invention increases the yield of 1,3-butadiene. With regard to Examples 2, 4 and 8 it also increases the selectivity to 1,3-butadiene. Particularly Example 2 shows a significantly increased selectivity to and improved yield of 1,3-butadiene compared to Comparative Example 1. Comparing Example 2 with Example 3 shows that increasing the reaction temperature from 350 to 375° C. increases conversion, which in view of a decrease in selectivity, still results in the same improved yield of 1,3-butadiene of 41% (compared to Comparative Example 1). The comparison of Examples 4 and 5, both using catalysts according to the invention with a lower specific surface area support of 190 m²/g, also shows that increasing the reaction temperature from 350 to 375° C. increases conversion, which despite a somewhat lower selectivity results in a high yield of 1,3-butadiene of 43%. The best yields of 43% and 44% of 1,3-butadiene, respectively, are achieved in Examples 5 and 8 according to the invention, with a low specific surface area support of 190 m²/g and a high reaction temperature of 375° C. Particularly Example 8, with a Cs₂O loading of 0.1 wt % based on the total weight of the catalyst, showed improved selectivity to 1,3-butadiene and strongly improved yield of 1,3-butadiene compared to Comparative Example 1.

The invention claimed is:

1. A process for the production of 1,3-butadiene, the process comprising
   i) contacting a feed comprising ethanol and acetaldehyde with a supported tantalum catalyst to obtain a raw product comprising 1,3-butadiene,
   wherein the catalyst is obtainable by a process comprising
      a) preparing a water-soluble tantalum precursor by reacting one or more tantalum compound(s) in aqueous solution and under oxidative conditions,
      b) aqueous impregnating a support with the water-soluble tantalum precursor obtained from step a),
      c) drying, and
      d) calcination.

2. The process of claim 1, wherein the supported tantalum catalyst has a tantalum content, calculated as Ta₂O₅ and based on the total weight of the catalyst, in a range of from 0.1 to 10 wt %.

3. The process of claim 2, wherein the tantalum content is in a range of from 2 to 3 wt%.

4. The process of claim 1, wherein the tantalum compound is selected from the group consisting of tantalum halides, tantalum hydroxide and tantalum oxalate.

5. The process of claim 4, wherein the tantalum compound is tantalum (V) hydroxide.

6. The process of claim 1, wherein the i) contacting takes place at a temperature in a range of from 200 to 500° C.

7. The process of claim 6, wherein the temperature is in a range of from 250 to 450° C.

8. The process of claim 1, wherein the i) contacting takes place at a weight hourly space velocity in a range of from 0.2 to 10 h⁻¹.

9. The process of claim 1, further comprising ii) separating the raw product at least into a first portion comprising 1,3-butadiene, a second portion comprising acetaldehyde and a third portion comprising ethanol.

10. The process of claim 9, wherein at least part of the second, of the third, or of the second and of the third portions is recycled into the feed.

11. The process of claim 1, wherein the i) contacting takes place in a continuous flow fixed bed reactor.

12. A process for the production of a supported tantalum catalyst, comprising the steps of
   a) preparing a water-soluble tantalum precursor by reacting one or more tantalum compound(s) in aqueous solution and under oxidative conditions,
   b) aqueous impregnating a support with the water-soluble tantalum precursor obtained from step a),
   c) drying, and
   d) calcination.

13. The process of claim 12, wherein the reacting in aqueous solution and under oxidative conditions comprises the presence of one or both of persulfate ion and hydrogen peroxide.

14. The process of claim 13, wherein the reacting in aqueous solution and under oxidative conditions comprises the presence of hydrogen peroxide.

15. The process of claim 12, wherein the reacting in aqueous solution is at a pH of greater than 7.

16. The process of claim 13, wherein the water-soluble tantalum precursor is prepared by
   a1) reacting said tantalum compound(s) with aqueous hydrogen peroxide, followed by reaction with one or both of aqueous ammonia and aqueous sodium hydroxide; or a2) reacting said tantalum compound(s) simultaneously with aqueous hydrogen peroxide and one or both of aqueous ammonia and aqueous sodium hydroxide.

17. The process of claim 16, wherein the weight ratio of tantalum to ammonia is in a range of from 3:1 to 1:1, wherein the weight ratio refers to tantalum as a metal and pure ammonia.

18. The process of claim 16, wherein the weight ratio of tantalum to hydrogen peroxide is in a range of from 1:10 to 1:40, wherein the weight ratio refers to tantalum as a metal and pure hydrogen peroxide.

19. The process of claim 12, wherein the support has a BET specific surface area in a range of from 130-550 $m^2/g$.

20. The process of claim 19, wherein the BET specific surface area is in a range of from 190 to 280 $m^2/g$.

21. A supported tantalum catalyst, obtainable by the process of claim 8.

22. The supported catalyst of claim 21, wherein the support is selected from ordered and non-ordered porous silica supports, aluminosilicate supports and other porous oxide-supports and mixtures thereof.

23. The supported tantalum catalyst of claim 21, further comprising caesium.

24. The supported tantalum catalyst of claim 23, wherein the caesium content of the catalyst is calculated as $Cs_2O$ and based on the total weight of the catalyst, and wherein the weight ratio of $Cs_2O$ to $Ta_2O_5$ in the catalyst is in a range of from 1:6 to 1:30.

\* \* \* \* \*

UNITED STATES PATENT AND TRADEMARK OFFICE
CERTIFICATE OF CORRECTION

PATENT NO. : 12,070,738 B2
APPLICATION NO. : 17/642885
DATED : August 27, 2024
INVENTOR(S) : Jankowiak et al.

Page 1 of 1

It is certified that error appears in the above-identified patent and that said Letters Patent is hereby corrected as shown below:

In the Claims

Column 13, Line 17, Claim 21, change "of claim 8." to --of claim 12.--

Signed and Sealed this
Twenty-fifth Day of March, 2025

Coke Morgan Stewart
*Acting Director of the United States Patent and Trademark Office*